United States Patent [19]

Ferrier

[11] Patent Number: 5,326,352
[45] Date of Patent: Jul. 5, 1994

[54] SELF ALIGNING AND QUICK COUPLING DEVICE FOR A PROSTHESIS

[76] Inventor: Lyle Ferrier, 3461 Burnside Rd., North Branch, Mich. 48461

[21] Appl. No.: 922,358

[22] Filed: Jul. 29, 1992

Related U.S. Application Data

[63] Continuation of Ser. No. 799,758, Nov. 27, 1991, abandoned, which is a continuation of Ser. No. 440,118, Nov. 22, 1989, abandoned.

[51] Int. Cl.$^5$ .............................. A61F 2/80; A61F 2/74
[52] U.S. Cl. ........................................ 623/38; 623/27
[58] Field of Search ............................ 623/31–33, 623/38, 57, 27

[56] References Cited

U.S. PATENT DOCUMENTS

| | | | |
|---|---|---|---|
| 1,302,336 | 4/1919 | Erickson | 623/38 |
| 3,273,168 | 9/1966 | Gardner et al. | 623/38 |
| 3,538,516 | 11/1970 | Bailey et al. | 623/38 |
| 3,649,968 | 3/1972 | Prahl | 623/38 |
| 3,707,731 | 1/1973 | Morgan | 623/38 |
| 4,007,496 | 2/1977 | Glabiszewski | 623/38 X |
| 4,564,365 | 1/1986 | Winer et al. | 623/38 X |
| 4,938,775 | 7/1990 | Morgan | 623/27 |

FOREIGN PATENT DOCUMENTS 847794 8/1952 Fed. Rep. of Germany ........ 623/38

Primary Examiner—Randall L. Green
Assistant Examiner—Elizabeth M. Burke
Attorney, Agent, or Firm—Gifford, Groh, Sprinkle, Patmore and Anderson

[57] ABSTRACT

An apparatus for use in attaching a leg prosthesis. The purpose of this coupling device is to allow for the quick attachment or detachment of the prosthesis without removal of the bucket portion which is left connected to the wearer by suction or by a belt. The device is both self aligning and quick coupling. One plate has a plug and the other plate has a socket into which the plug fits. A threaded pin joins the two plates and forces the two plates, which are deliberately misaligned, together.

6 Claims, 2 Drawing Sheets

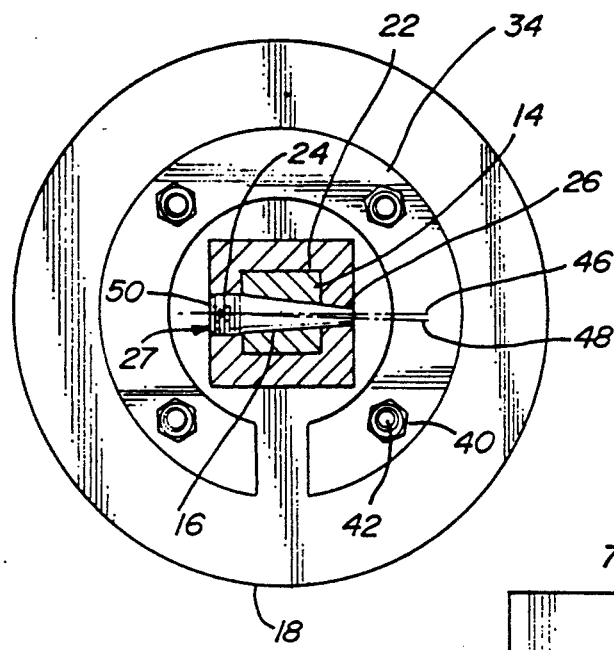
Fig-4
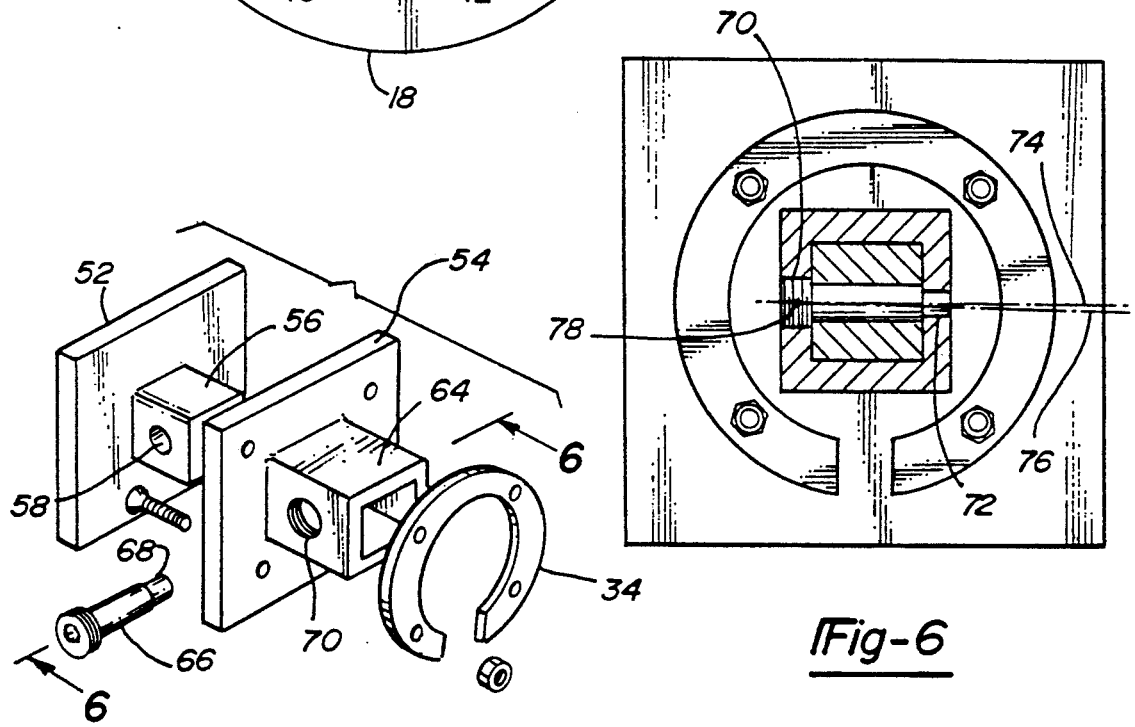
Fig-5
Fig-6

SELF ALIGNING AND QUICK COUPLING DEVICE FOR A PROSTHESIS

This is a Ser. No. 07/799,758 filed on Nov. 27, 1991, now abandoned, which is a continuation of co-pending application Ser. No. 07/440,118 filed Nov. 22, 1989 now abandoned.

BACKGROUND OF THE INVENTION

I. Field of the Invention

This invention relates to a quick coupler, particularly for a leg prosthesis, which coupler is self-aligning in use. The invention allows for rapid and convenient removal or attachment of a prosthesis to a wearer mounted bucket without removal of the entire apparatus.

II. Description of the Prior Art

Various prosthesic attachments have been devised typically to attach a temporary artificial limb to a wearer. For example, U.S. Pat. No. 3,262,131 discloses an artificial leg with detachable stump support sock.

This device is designed to provide a simple lightweight artificial leg and is to be used for an emergency leg or as a temporary convenience. It is apparently not intended for a complex artificial limb.

U.S. Pat. No. 3,461,464 discloses an artificial limb having interchangeable leg sections and length adjusting means. This device allows for the changing of a peg or an artificial foot. This device requires adjustment in a longitudinal plane at a distance away from the mounting portion.

SUMMARY OF THE PRESENT INVENTION

The above noted disadvantages are overcome by the present invention. The quickly connected apparatus allows the wearer greater flexibility and comfort. The portion with the prosthesis can be removed while the bucket portion is still attached to the wearer. This allows the wearer to remove the prosthesis during periods of immobility such as riding in a vehicle and allows the wearer to exercise the stump to help circulation. The prosthesis if mounted to a leg can be readily removed through a trouser leg instead of fully undressing.

The quickness and ease by which the prosthesis is removable allows a wearer greater options. Some of these could be replacing the prosthesis with a peg or some other device to protect the permanent prosthesis from damage during showering, wading or immersing in contaminants. The leg prosthesis can also be replaced by a kneeling pad, if so desired.

BRIEF DESCRIPTION OF THE DRAWINGS

One exemplary embodiment and one modified arrangement will be described in the following with reference being made to the drawings, wherein:

FIG. 4 is a cross-sectional view of FIG. 3 along line 4—4; and

FIG. 5 is a perspective view of a modified arrangement.

FIG. 6 is a cross-sectional view of FIG. 5 along line 6—6.

DETAILED DESCRIPTION OF THE PREFERRED EMBODIMENT

Figure 1:
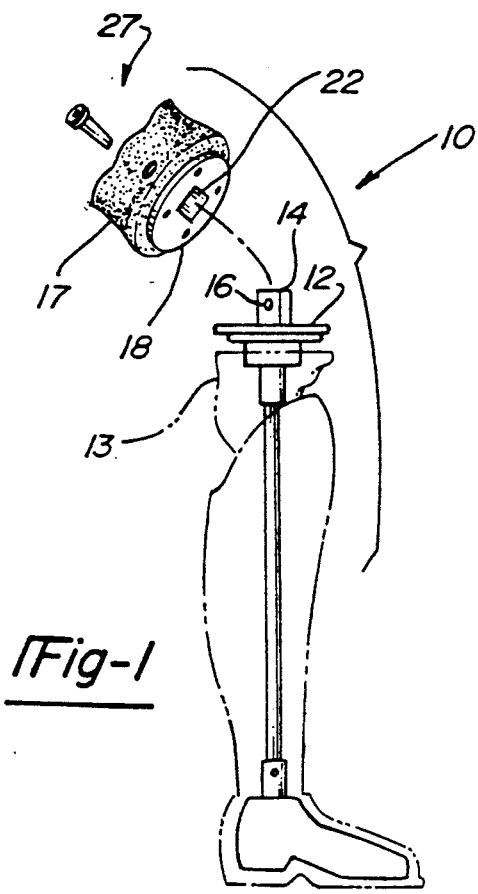
FIG. 1 is a perspective illustration of the preferred connector as used.

Refering first to FIG. 1, the coupler is shown in the environment in which it is intended to be used. The plate 18 having a socket opening 22 is attached to a stump bucket 17 which is then held to the wearer by a number of possible methods. The mating plate 12 with plug 14 is attached to a prosthesic device 13.

Figure 2:
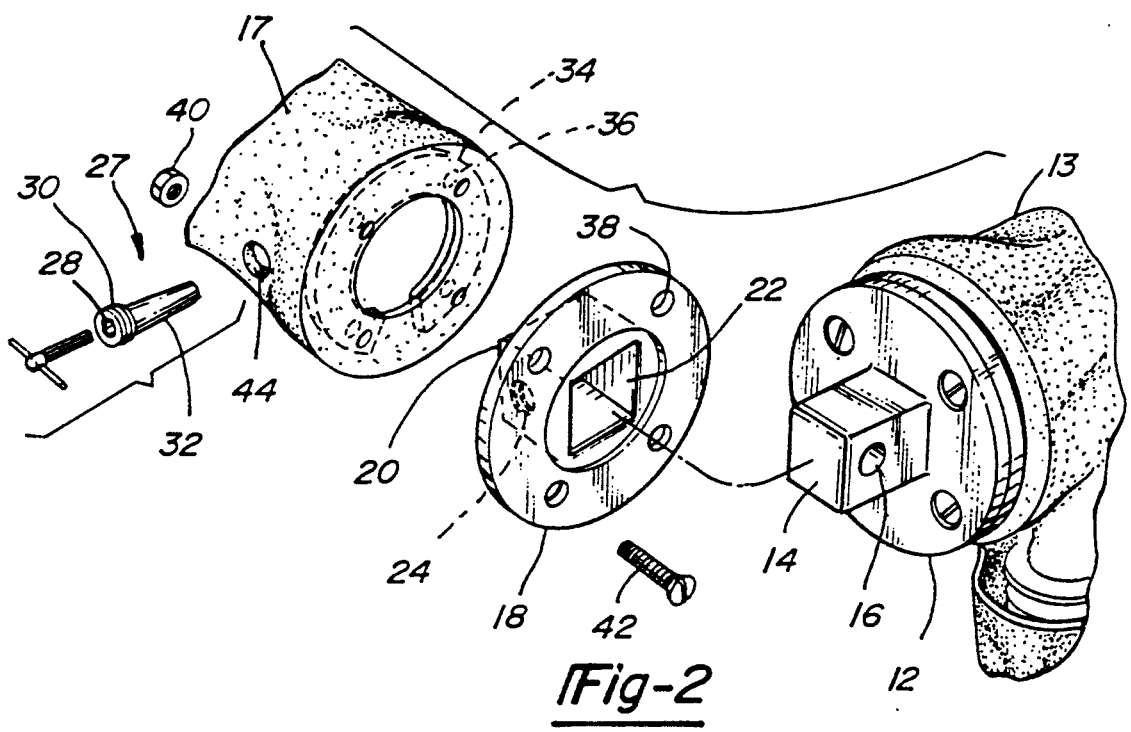
FIG. 2 is an perspective hinged illustration of the coupler.

Now referring to FIG. 2, the coupler is there shown with a round plate 12 which has a plug 14 mounted or integral to the pl ate. Some details are better shown in FIG. 4. The plate is attached to a prosthesic device 13. The plug has a frustoconical bore 16 through it.

A second round pl ate 18 has a socket 20 mounted or integral to the plate. The socket 20 has an interior opening 22 dimensioned to accept the plug 14 of the first plate. The socket 20 has a threaded bore 24 through one wall and a bore 26 on the opposite wall of the socket. The second plate is attached to the stump bucket 117 which is attached to the user.

A split collar ring 34 i s used to attach the stump bucket to the second round plate 18. The ring has four holes 36 equally spaced that match four equally spaced holes 38 in the second round plate.

The stump bucket is held between the pl ate and the ring, the holes are lined up and the bolts 42 and the nuts 40 are tightened to secure the assembly. An access hole 44 is provided i n the bucket so that the pin 27 shown in FIGS. 1 and 2 can be inserted and removed.

The pin 27 is of nylon and has an Allen head socket 28, a tapered body 32 and threads 30 on the diameter of the head that match the receiving threaded portion 24 on the socket.

Figure 3:
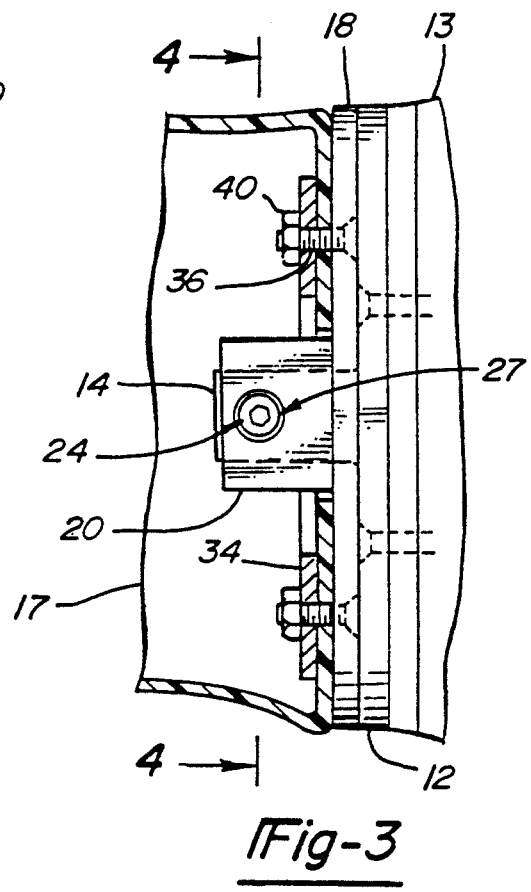
FIG. 3 is a side view of FIG. 2.

FIG. 3 shows the coupler 10 with the plates 12, 18 mated together so that the plug 14 fits into the socket 20 with the bore 16 of the plug in line with the bores 24 and 26 of the socket 20. The recessed Allen head socket 28 of the pin is shown mounted in bore 24. The stump bucket 17 is shown cut away.

FIG. 4 is a cross-sectional view of the assembled connector. The plug 14 is shown inserted into the socket 22 and the pin 27 is assembled to hold and lock the components together.

The centerline 46 of the plug bore 16 is not on the centerline 48 of the socket threaded bore 24 and the tapered bore 26. Bore centerlines 46 and 48 originate from the same point 50 in the threaded bore 24.

The centerlines are deliberately misaligned to cause the two plates to be forced together when the pin is entered into the threaded plate socket bore and then tightened. The misaligned bore 16 is positioned so as to permit the pin 27 and the pin threads 29 to engage properly with threaded portion of the socket bore 24 as the pin threads are turned into the bore threads. A forced alignment results with the first plate 12 mating solidly and stably with the second plate 18.

Referring now to FIG. 5 and 6, a modified arrangement is described. The plates 52, 54 serve the same purpose as plates 12, 18 in the preferred embodiment. The plug 56 mounted or integral to plate 52 contains a bore 58. The socket 64 mounted to or integral with plate 54 is basically as described in FIG. 2.

The socket has a larger threaded bore 70 and a smaller bore 72 on the opposite socket wall. In this version, the pin 66 is a shoulder pin with a straight diameter body style with a smaller diameter cylindrical point 68. This pin is also made from nylon.

FIG. 6 is a cross-sectional view of the modified coupler shown in FIG. 5. The shoulder pin 66 has threads which match the threads of the socket to start the attachment.

The centerline 74 of the plug bore 58 and the centerline 76 of the bores 70 and 72 originate from the same origin point 78 in bore 70 and are misaligned in the same manner and for the same purpose as described in FIG. 4.

Having described my invention, however, many modifications thereto will become apparent to those skilled in the art to which it pertains without deviation from the spirit of the invention as defined by the scope of the appended claims.

I claim:

1. A prosthetic coupling, comprising:
   a prosthetic socket;
   an artificial limb, removably attached to said prosthetic socket to permit said socket to remain attached to a wearer's limb stump while the artificial limb is removed;
   a first plate having means for attaching to said socket and a second plate having means for attaching to said artificial limb, each of said plates having a attachment end, said plates being positioned to be in attachment end-to-attachment end alignment for attaching said artificial limb to said socket;
   one of said attachment ends including a protrusion, said protrusion having a mating surface, and the other of said attachment ends including an aperture for receiving said protrusion, said aperture having a mating surface, said mating surface of said aperture being configured to mate with said mating surface of said protrusion, and
   a pin inserted through a side of said socket and into said protrusion whenever said protrusion is disposed within said aperture, said pin locking said attachment ends to each other and being operable to force the attachment end of said first plate toward and maintaining engagement with the attachment end of said second plate to attach the artificial limb to the socket, said pin causing said first plate to be misaligned with respect said second plate to assist in tightening said first plate against said second plate.

2. The coupling as defined in claim 1 and in which said protrusion has defined therein a tapered, pin receiving aperture.

3. The coupling as defined in claim 2 and in which said pin includes a tapered surface, said tapered surface being matable with said tapered, pin-receiving aperture defined in said protrusion.

4. The coupling as defined in claim 3 and in which said attachment end having said protrusion-receiving aperture further includes a pin-receiving aperture.

5. The coupling as defined in claim 4 and wherein said pin-receiving aperture of said protrusion and said pin-receiving aperture of said attachment end having said protrusion-receiving aperture are misaligned.

6. A coupling for attaching a prosthetic socket to an artificial limb to permit the socket to remain attached to a wearer's limb stump while the artificial limb is removed, said coupling comprising:
   a first plate, said first plate having an attachment end, said first plate having means for fastening to the socket and a second plate, said second plate having an attachment end, said second plate having means for fastening to the artificial limb, said plates being positioned to be in end-to-end alignment when the artificial limb is properly positioned with respect to said socket;
   attachment means for selectively attaching said attachment end of said first plate to said attachment end of said second plate to thereby mount the artificial limb to said socket;
   said attachment means comprising a projection provided on one of said ends, and a projection-receiving aperture provided on the other of said ends;
   each of said projection and said projection-receiving apertures being provided with a pin-receiving aperture so that there are at least two pin-receiving apertures, said attachment means further comprising a pin for removable placement into said pin-receiving apertures, said pin extending through a portion of said first plate and into said projection for locking said first plate to said second plate.

* * * * *

UNITED STATES PATENT AND TRADEMARK OFFICE
CERTIFICATE OF CORRECTION

PATENT NO. : 5,326,352
DATED : July 5, 1994
INVENTOR(S) : Lyle Ferrier

It is certified that error appears in the above-identified patent and that said Letters Patent is hereby corrected as shown below:

Column 1, line 5, before "Ser. No." insert

-- continuation of --;

Column 2, line 10, delete "there shown" and insert

-- thereshown --;

Column 2, line 12, delete "pl ate" and insert -- plate --;

Column 2, line 15, delete "pl ate" and insert -- plate --;

Column 2, line 20, delete "117" and insert -- 17 --;

Column 2, line 22 delete " i s " and insert -- is --;

Column 2, line 26, delete "pl ate" and insert -- plate --;

Column 2, line 29, after "provided" delete "i n" and insert -- in --;

UNITED STATES PATENT AND TRADEMARK OFFICE
CERTIFICATE OF CORRECTION

PATENT NO. : 5,326,352
DATED : July 5, 1994
INVENTOR(S) : Lyle Ferrier

It is certified that error appears in the above-indentified patent and that said Letters Patent is hereby corrected as shown below:

Column 3, line 24, delete "a" and insert -- an --.

Signed and Sealed this

Twentieth Day of September, 1994

Attest:

BRUCE LEHMAN

Attesting Officer    Commissioner of Patents and Trademarks